(12) United States Patent
Huang et al.

(10) Patent No.: US 10,252,042 B2
(45) Date of Patent: Apr. 9, 2019

(54) TRANSDERMAL MICRONEEDLE UNIT AND TRANSDERMAL MICRONEEDLE DRUG DELIVERY DEVICE HAVING THE SAME

(71) Applicants: Jung-Tang Huang, Taipei (TW); JIU-LONG INDUSTRIAL CO., LTD., New Taipei (TW)

(72) Inventors: Jung-Tang Huang, Taipei (TW); King-Chun Chang, New Taipei (TW)

(73) Assignees: Jung-Tang Huang, Taipei (TW); JIU-LONG INDUSTRIAL CO., LTD., New Taipei (TW)

( * ) Notice: Subject to any disclaimer, the term of this patent is extended or adjusted under 35 U.S.C. 154(b) by 211 days.

(21) Appl. No.: 15/005,332

(22) Filed: Jan. 25, 2016

(65) Prior Publication Data

US 2016/0220802 A1      Aug. 4, 2016

(30) Foreign Application Priority Data

Jan. 29, 2015 (TW) .............................. 104103104 A

(51) Int. Cl.
    *A61M 37/00* (2006.01)
(52) U.S. Cl.
    CPC . *A61M 37/0015* (2013.01); *A61M 2037/0023* (2013.01); *A61M 2037/0053* (2013.01)
(58) Field of Classification Search
    CPC ...... A61M 37/0015; A61M 2037/0023; A61M 2037/003; A61M 2037/0038; A61M 2037/0046; A61M 2037/0053; A61M 2037/0061
    USPC .................................................. 604/173, 46
    See application file for complete search history.

(56) References Cited

U.S. PATENT DOCUMENTS

| 2003/0199810 A1* | 10/2003 | Trautman | A61M 37/0015 604/46 |
| 2008/0015494 A1* | 1/2008 | Santini, Jr. | A61M 5/1409 604/65 |
| 2011/0295230 A1* | 12/2011 | O'Dea | A61M 37/0015 604/506 |
| 2014/0052067 A1* | 2/2014 | Sausse | A61M 37/0015 604/173 |
| 2015/0208970 A1* | 7/2015 | Huang | A61B 5/685 600/345 |
| 2015/0208984 A1* | 7/2015 | Huang | A61B 5/685 600/393 |

(Continued)

FOREIGN PATENT DOCUMENTS

WO      WO 2015005359 A1 *   1/2015    ........ A61M 37/0015

*Primary Examiner* — Kevin C Sirmons
*Assistant Examiner* — Leah J Swanson
(74) *Attorney, Agent, or Firm* — Chun-Ming Shih; HDLS IPR SERVICES

(57) ABSTRACT

The invention relates to a transdermal microneedle unit and a transdermal microneedle drug delivery device comprising the transdermal microneedle unit. The transdermal microneedle unit comprises a plurality of sheets stacked with each, each the sheet having at least one through hole defined thereon and a barbule arranged at the peripheral of the through hole, wherein the through hole on one sheet is penetrated by the barbules of other sheets and the barbules being juxtaposed to form at least one triangular pyramidal transdermal microneedle. The transdermal microneedle drug delivery device comprises a substrate, a transdermal microneedle unit, a union joint and an injection syringe.

7 Claims, 15 Drawing Sheets

(56) References Cited

U.S. PATENT DOCUMENTS

2015/0208985 A1* 7/2015 Huang ............ A61B 5/150022
600/348

* cited by examiner

TRANSDERMAL MICRONEEDLE UNIT AND TRANSDERMAL MICRONEEDLE DRUG DELIVERY DEVICE HAVING THE SAME

BACKGROUND OF THE INVENTION

Field of the Invention

The present invention relates to a transdermal drug delivery device, especially to a transdermal drug delivery device which may deliver injectable drug to the subcutaneous tissue for treatment.

Description of the Related Art

The global injectable drug delivery market was valued at $22.5 billion in 2012; it is expected to reach $43.3 billion by 2017 at a CAGR of 14.0% from 2012 to 2017, according to the report of Injectable Drug Delivery Market by Formulations, Devices & Therapeutics—Global Forecasts to 2017. The injectable drug delivery technologies market is broadly categorized into two major segments, namely, devices technologies and formulation technologies. Based on product, the injectable drug delivery devices technologies market is further categorized into conventional injection devices, self injection devices, and others (microneedles, nanoneedles and blunt needle injections), while injectable drug delivery formulation technologies market is categorized into conventional drug delivery formulations and novel drug delivery formulations. Conventional injection devices segment accounted for the largest share of the overall injectable drug delivery technologies market in 2012.

In addition, the market is segmented on the basis of its therapeutic applications such as auto immune diseases, hormonal imbalances, oncology, orphan/rare diseases (Hemophilia, Ribose-5-phosphate isomerase deficiency (RPI deficiency), Cystic Fibrosis, and Wilson's disease) and others (pain management, allergies, hepatitis C, and aesthetic treatment). Hormonal disorders commanded the largest share of 50.0% of the global injectable drug delivery market in 2012; it is expected to grow at a CAGR of 13.9% to reach $21.6 billion by 2017. However, auto-immune diseases are the fastest growing segment of this market due to the advent of biologics (tumor necrosis factor (TNF) and Interleukin 1 (IL-1)) and improving patient compliance by the development of self injection devices. As per The American Autoimmune Related Diseases Association, 50 million Americans or 20% of the population or one in five people, are living and managing with auto immune diseases during the year 2013.

The major geographic markets of the injectable drug delivery technologies are North America, Europe, Asia-Pacific, and Rest of the World (RoW). North America dominates the market, followed by Europe. However, Asian and Latin American countries represent the fastest growing markets due to growing number of cancer and diabetes incidences.

In addition, the outbreaks of highly pathogenic avian influenza in Asia for the past few years and spread of the disease worldwide highlight the need to redefine conventional immunization approaches and establish effective mass vaccination strategies to face global pandemics. Vaccination is one of approaches to fight infectious diseases and deaths. The conventional vaccination approach is an invasive method that has disadvantages such as sometimes it is painful for the person, it is required to carry out the injection by medical personnel or professional personnel, the injectable drug delivery is always connected with a risk of infection, and storage and transportation of the vaccine. Transcutaneous immunization (TCI) is a novel route for vaccination, which uses the topical application of vaccine antigens on the skin that can enhance medicine effectiveness and improve patient compliance.

Therefore, the transdermal drug delivery device is worth further developing. Typically, the transdermal drug delivery device has microneedle array that is formed by high precision machining technology, e.g., precision stamping, ion etching, sand blast laser, X-ray laser cutting, lithography, coupled plasma, electrocasting technology. The length of the microneedles typically is about tens of micrometers. The transdermal microneedle drug delivery device with minimally invasive piercing can effectively reduce the pain of the users to achieve an injection without pain almost.

In current application, cosmetic surgery using derma roller, also called microneedling therapy system (MTS), is a minimally invasive skin-rejuvenation procedure that involves the use of a device that contains fine needles. The needles are used to puncture the skin to create a controlled skin injury. Each puncture creates a channel that triggers the body to fill these microscopic wounds by producing new collagen and elastin. Through the process of neovascularization and neocollagenesis, there is improvement in skin texture and firmness, as well as reduction in scars, pore size, and stretch marks.

The traditional medical drug delivery technology has its limitations, such as oral dosing is the most convenient and cheapest way, but the medical drug absorption is interfered by diet and other drug. Also, the absorbed dose of the medical drug is reduced due to hepatic metabolism. As to intravenous injection, the drug delivery may be fast and accurate, but it is required to provide by the professional and painful for patients. In medical applications, the transdermal drug delivery device with microneedle array can deliver drugs through the skin, and can penetrate drugs through the skin into the bloodstream, is a very attractive and new drug delivery technology.

The array-arranged microneedles of a transdermal drug delivery device can be manufactured with standard semiconductor process such as photolithograph process and etching process. The related art disclosed a process for manufacturing silicon microneedles. Firstly a silicon wafer with a first patterned photoresist layer is prepared. Next, a through hole is defined on the wafer by anisotropic etching. Afterward, a chromium layer is coated on the wafer and a second patterned photoresist layer is formed atop the through hole to function as circular etching mask. Next, the wafer is then etched to form outer tapered wall for the microneedles. However, the silicon-based microneedles are brittle and tend to break when the microneedles prick through user's skin.

Alternatively, hollow microneedles with resin barbules are proposed, where the barbules are drilled by laser processing. Firstly, sheet with barbules is formed by extruding polyimide or polyether ether ketone, and then the barbules are drilled by laser to form hollow microneedles. However, the microneedles have compact size such that the barbules may have ragged edge after extrusion. Moreover, it is difficult to form a hollow microneedle with off-axis through hole or central through hole having uniform inner diameter by laser processing.

In summary, there is a need to provide a transdermal drug delivery device which may deliver injectable drug to the subcutaneous tissue for treatment. The microneedle of the transdermal drug delivery device can be kept intact after the microneedle pricks user's skin for drug delivery.

SUMMARY OF THE INVENTION

One object of the present invention is to provide a transdermal microneedle unit, where the transdermal microneedle unit has microneedles made by punching or etching to have sufficient mechanical strength. The microneedle is formed by barbules having different aspects to juxtapose each other after the sheets are stacked together, and the tips of the barbules are in polygon arrangement from top view. The microneedle can be kept intact after the microneedle pricks user's skin for drug delivery.

Accordingly, the present invention provides a transdermal microneedle unit comprising: a plurality of sheets stacked with each other, each of sheets having a through hole defined thereon and a barbule arranged at the peripheral of the through hole, wherein the through hole on one sheet is penetrated by the barbules of other sheets, and all the barbules juxtapose with each other to form a transdermal microneedle, and the tips of the barbules are in polygon arrangement from top view.

In an aspect of the invention, the transdermal microneedle unit comprises a first sheet and a second sheet stacked with the first sheet. The first sheet has a first through hole defined thereon, and a first barbule at peripheral of the first through hole. The second sheet has a second through hole defined thereon, and a second barbule at peripheral of the second through hole, where the second barbule penetrates the first through hole to juxtapose the first barbule.

In another aspect of the invention, the transdermal microneedle unit comprises a first sheet, a second sheet and a third sheet stacked with each other. The first sheet has a first through hole defined thereon, and a first barbule at peripheral of the first through hole. The second sheet has a second through hole defined thereon, and a second barbule at peripheral of the second through hole. The third sheet has a third through hole defined thereon, and a third barbule at peripheral of the third through hole. The second barbule and the third barbule penetrates the first through hole to juxtapose the first barbule, and the tips of the barbules are in triangular arrangement from top view.

In still another aspect of the invention, the transdermal microneedle unit comprises a first sheet, a second sheet, a third sheet and a fourth sheet stacked with each other. The first sheet has a first through hole defined thereon, and a first barbule at peripheral of the first through hole. The second sheet has a second through hole defined thereon, and a second barbule at peripheral of the second through hole. The third sheet has a third through hole defined thereon, and a third barbule at peripheral of the third through hole. The fourth sheet has a fourth through hole defined thereon, and a fourth barbule at peripheral of the fourth through hole. The second barbule, the third barbule and the fourth barbule penetrates the first through hole to juxtapose the first barbule, and the tips of the barbules are in rectangular arrangement from top view.

The transdermal microneedle unit has a first barbule comprising a tip and a base. The tips of those barbules, after the sheets are stacked together, are not at the same altitudes to form an opening for medications passing through. Namely, some barbules pass more through holes than other barbules. Alternatively, the height of the barbules can be such designed, based on the stacked order of sheets, that the tips of those barbules, after the sheets are stacked together, are at the same altitudes to form an opening by cutting at least one tip of the barbule for medications passing through.

The barbules of the transdermal microneedle are made by punching, etching, molding, micromachining, hot forming or cold forming. The barbule of the transdermal microneedle has a material selected from stainless steel, nickel, nickel alloy, titanium, titanium alloy, carbon nanotube, silicon or resin. In case that the biological incompatible material is used, the surface of the barbule may be coated with a layer of biological compatible material.

In order to achieve the object of the present invention, the present invention provides a transdermal microneedle unit comprising a plurality of sheets stacked with each other, each of sheets having array-arranged through holes defined thereon and a barbule arranged at the peripheral of each the through holes in array arrangement, wherein the array-arranged through holes on one sheet is penetrated by the barbules of other sheets, and all the barbules juxtapose with each other to form a transdermal microneedle, and the tips of the barbules are in polygon arrangement from top view. Every barbule has the same aspect on a sheet, or the barbules in different row have different aspects on a sheet. The transdermal microneedle unit is combined with a substrate, and there is a space surrounded by the barbules of the transdermal microneedle unit for embedding with a low flowability medication.

Another object of the present invention is to provide a transdermal microneedle drug delivery device. The transdermal microneedle drug delivery device may deliver injectable drug to the subcutaneous tissue for treatment.

Accordingly, the present invention provides a transdermal microneedle drug delivery device comprising a substrate, a transdermal microneedle unit and a union joint. The transdermal microneedle unit is provided on the substrate, and the transdermal microneedle unit comprises a plurality of sheets stacked with each other, each of sheets having at least one through hole defined thereon and a barbule arranged at the peripheral of the through hole, wherein the through hole on one sheet is penetrated by the barbules of other sheets, and all the barbules juxtapose with each other to form a transdermal microneedle, and the tips of the barbules are in polygon arrangement from top view. The transdermal microneedles of the transdermal microneedle unit may be arranged in array arrangement. The union joint is connected with the substrate by an end thereof, and connected with an injection syringe by another end to apply the medications into skin. The union joint has a circular groove in the front surface of an end thereof, and a O-ring is provided in the circular groove of the union joint in order to avoid a leakage of medications.

The transdermal microneedle drug delivery device of the invention further comprises a gasket which has at least one projecting part for sealing an opening on the bottom of the transdermal microneedle of the transdermal microneedle unit. The gasket is an insert molding article formed by injection molding. Alternatively, the gasket is molded independently, thereafter the gasket is combined with the transdermal microneedle unit.

In the transdermal microneedle drug delivery device of the invention, the substrate has a plurality of latches, and each of latches has an entrance at an end thereof, and the union joint has a plurality of projections at a side surface of an end, and the union joint is engaged with the substrate by screwing each of projections into the corresponding entrances of the latches.

The transdermal microneedle drug delivery device further comprises an injection syringe including a plunger, in which the injection syringe has a connecting end for connecting with another end of the union joint, and the plunger is pushed along inside a cylindrical tube of the injection syringe to apply the medications into skin. The transdermal microneedle drug delivery device with minimally invasive piercing can effectively reduce the pain of the users to achieve an injection without pain almost.

In addition, the transdermal microneedle drug delivery device further comprises a micropump and a micro control unit, in which the micropump is connected with another end of the union joint, and the micropump is driven by a signal produced from the micro control unit to apply the medications into skin. The transdermal microneedle drug delivery device with minimally invasive piercing can effectively reduce the pain of the users to achieve an injection without pain almost.

Compared to the prior art, the transdermal microneedle unit of the invention has microneedles made by punching or etching to have sufficient mechanical strength. The microneedle can be kept intact after the microneedle pricks user's skin for drug delivery. In addition, the method for manufacturing the transdermal microneedle unit is simple for mass production.

DETAILED DESCRIPTION OF THE INVENTION

Figure 1:
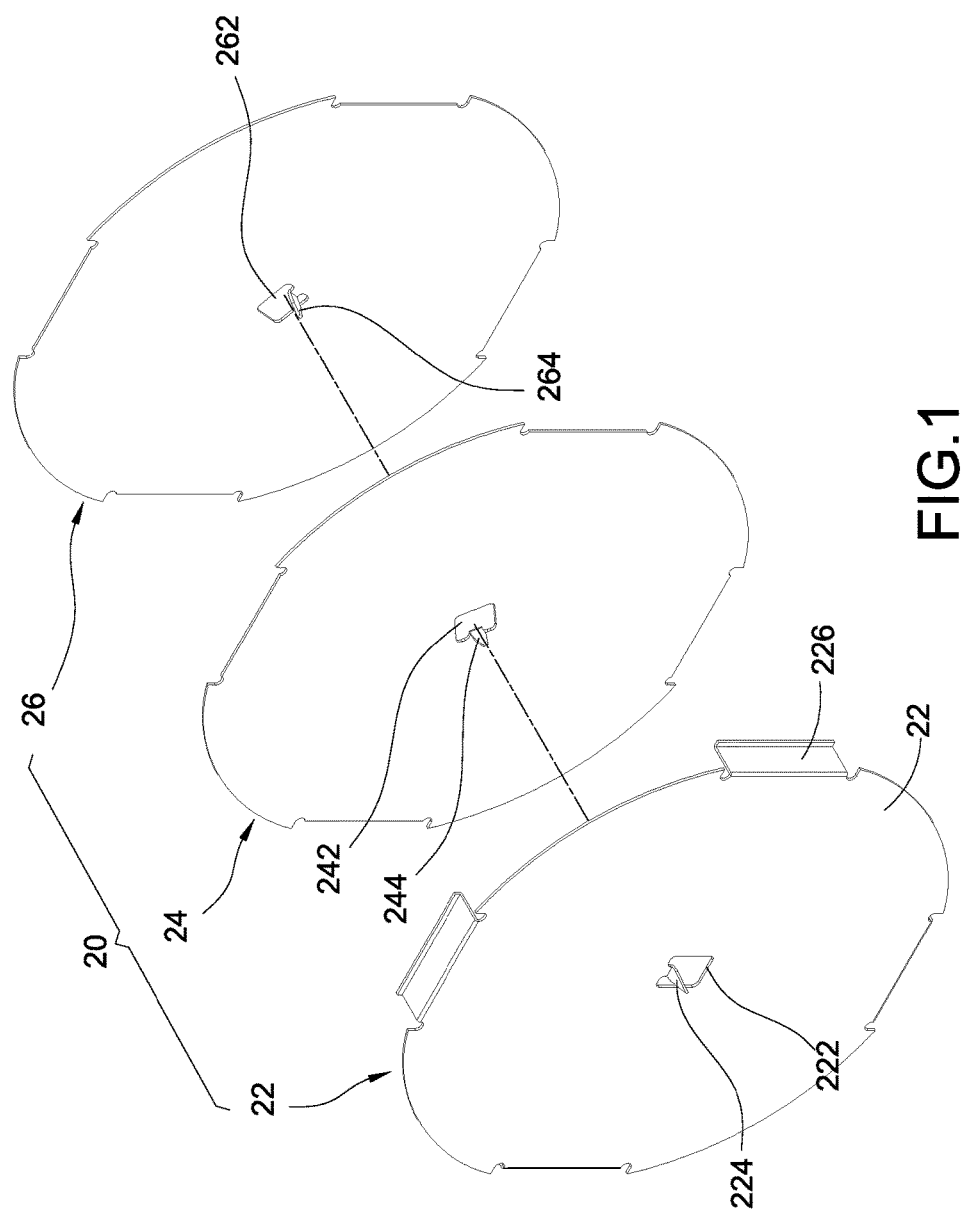
FIG. 1 shows an exploded view of the transdermal microneedle unit according to an embodiment of the present invention from a front viewing direction.

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

FIG. 1 shows an exploded view of the transdermal microneedle unit according to an embodiment of the present invention from a front viewing direction. According to FIG. 1, the transdermal microneedle unit 20 comprises a first sheet 22, a second sheet 24 and a third sheet 26 stacked with each other. The first sheet 22 has a first through hole 222 defined thereon, and a first barbule 224 at peripheral of the first through hole 222. The second sheet 24 has a second through hole 242 defined thereon, and a second barbule 244 at peripheral of the second through hole 242. The third sheet 26 has a third through hole 262 defined thereon, and a third barbule 264 at peripheral of the third through hole 262. The second barbule 244 and the third barbule 264 penetrates the first through hole 222 to juxtapose the first barbule 224, and the tips of the barbules are in isosceles triangular arrangement from top view. Although the embodiment of FIG. 1 illustrates the transdermal microneedle unit is formed by three sheets each has a through hole and a barbule stacked with each other, in the other embodiments it may be formed by two sheets each has a through hole and a barbule stacked with each other, where the second barbule penetrates the first through hole to juxtapose the first barbule, or it may be formed by four sheets each has a through hole and a barbule stacked with each other, where the second barbule, the third barbule and the fourth barbule penetrate the first through hole to juxtapose the first barbule, and the tips of the barbules are in rectangular arrangement from top view.

With reference to FIGS. 2 to 5, FIG. 2 is a top view of the transdermal microneedle of the transdermal microneedle unit according to an embodiment of the present invention. According to FIG. 2, the transdermal microneedle unit 20 comprises a first sheet 22 and a second sheet 24 stacked with the first sheet 22. The first sheet 22 has a first through hole 222 defined thereon, and a first barbule 224 at peripheral of the first through hole 222. The second sheet 24 has a second through hole 242 defined thereon, and a second barbule 244 at peripheral of the second through hole 242, where the second barbule 244 penetrates the first through hole 222 to juxtapose the first barbule 224.

Figure 3:
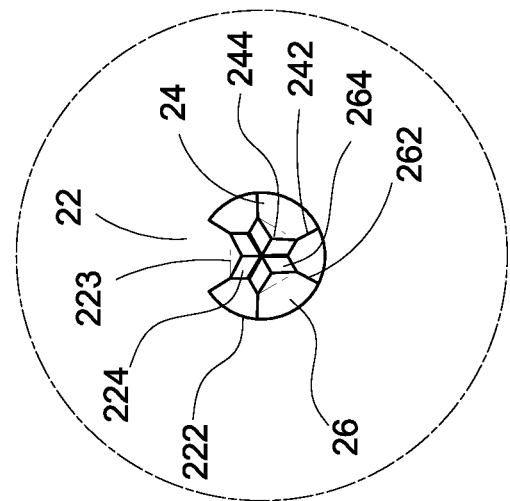
FIG. 3 is a top view of the transdermal microneedle of the transdermal microneedle unit according to another embodiment of the present invention.
Figure 2:
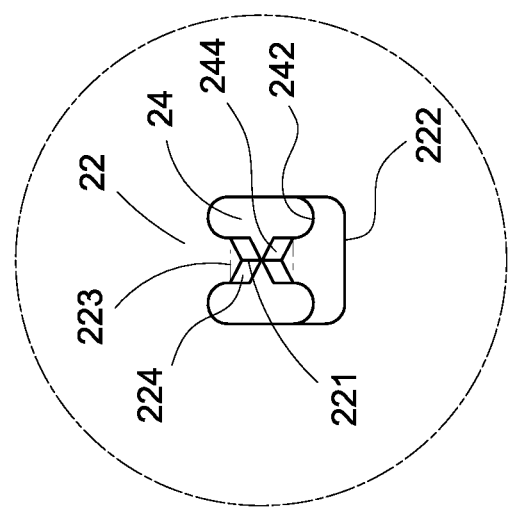
FIG. 2 is a top view of the transdermal microneedle of the transdermal microneedle unit according to an embodiment of the present invention.

FIG. 3 is a top view of the transdermal microneedle of the transdermal microneedle unit according to another embodiment of the present invention. According to FIG. 3, the transdermal microneedle unit 20 comprises a first sheet 22, a second sheet 24 and a third sheet 26 stacked with each other. The first sheet 22 has a first through hole 222 defined thereon, and a first barbule 224 at peripheral of the first through hole 222. The second sheet 24 has a second through hole 242 defined thereon, and a second barbule 244 at peripheral of the second through hole 242. The third sheet 26 has a third through hole 262 defined thereon, and a third barbule 264 at peripheral of the third through hole 262. The second barbule 244 and the third barbule 264 penetrates the first through hole 222 to juxtapose the first barbule 224, and the tips of the barbules are in right triangular arrangement from top view.

Figure 4:
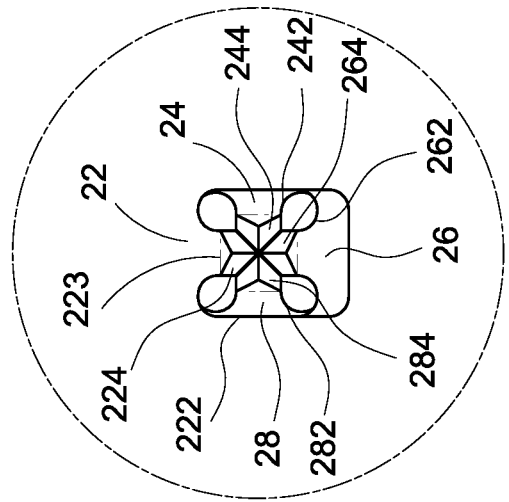
FIG. 4 is a top view of the transdermal microneedle of the transdermal microneedle unit according to still another embodiment of the present invention.

FIG. 4 is a top view of the transdermal microneedle of the transdermal microneedle unit according to still another embodiment of the present invention. According to FIG. 4, the transdermal microneedle unit 20 comprises a first sheet 22, a second sheet 24 and a third sheet 26 stacked with each other. The first sheet 22 has a first through hole 222 defined thereon, and a first barbule 224 at peripheral of the first through hole 222. The second sheet 24 has a second through hole 242 defined thereon, and a second barbule 244 at peripheral of the second through hole 242. The third sheet 26 has a third through hole 262 defined thereon, and a third barbule 264 at peripheral of the third through hole 262. The second barbule 244 and the third barbule 264 penetrates the first through hole 222 to juxtapose the first barbule 224, and the tips of the barbules are in isosceles triangular arrangement from top view.

Figure 5:
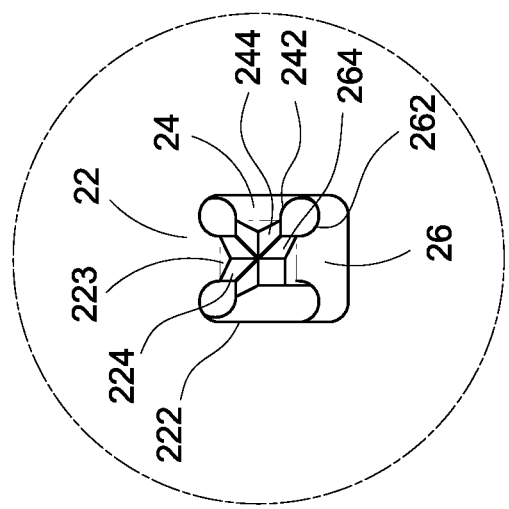
FIG. 5 is a top view of the transdermal microneedle of the transdermal microneedle unit according to further another embodiment of the present invention.

FIG. 5 is a top view of the transdermal microneedle of the transdermal microneedle unit according to further another embodiment of the present invention. According to FIG. 5, the transdermal microneedle unit 20 comprises a first sheet 22, a second sheet 24, a third sheet 26 and a fourth sheet 28 stacked with each other. The first sheet 22 has a first through hole 222 defined thereon, and a first barbule 224 at peripheral of the first through hole 222. The second sheet 24 has a second through hole 242 defined thereon, and a second barbule 244 at peripheral of the second through hole 242. The third sheet 26 has a third through hole 262 defined thereon, and a third barbule 264 at peripheral of the third through hole 262. The fourth sheet 28 has a fourth through hole 282 defined thereon, and a fourth barbule 284 at peripheral of the fourth through hole 282. The second barbule 244, the third barbule 264 and the fourth barbule 284 penetrates the first through hole 222 to juxtapose the first barbule 224, and the tips of the barbules are in rectangular arrangement from top view.

With the four embodiments as shown in FIGS. 2 to 5, the transdermal microneedle unit 20 has a first barbule 224 comprising a tip 221 and a base 223. The tips of those barbules, after the sheets are stacked together, are not at the same altitudes to form an opening. Namely, some barbules pass more through holes than other barbules. Alternatively, the height of the barbules can be such designed, based on the stacked order of sheets, that the tips of those barbules, after the sheets are stacked together, are at the same altitudes to form an opening by cutting at least one tip of the barbule.

Please refer to FIG. 1 again. In an embodiment, the barbules 224, 244, 264 of the transdermal microneedle unit 20 can be made by punching, etching, molding, micromachining, hot forming or cold forming process. The material of the barbules 224, 244, 264 is selected from the group consisting of stainless steel, nickel, nickel alloy, titanium, titanium alloy, carbon nanotube, and silicon. Alternatively, the material of the barbules can also be selected from the group consisting of polycarbonate, polymethacrylic acid copolymer, ethylene vinyl acetate copolymer, polytetrafluoroethylene, and polyester. Also, the barbules 224, 244, 264 of the transdermal microneedle unit 20 can be made by injection molding or hot pressing. Moreover, the height of the barbules 224, 244, 264 is 300-2500 micrometers; the base width of the barbules 224, 244, 264 is 150-650 micrometers. The separation between tips of the barbules 224, 244, 264 is 500-2000 micrometers. The opening of the microneedles is off-axis with an equivalent diameter of 20-100 micrometers.

Figure 6:
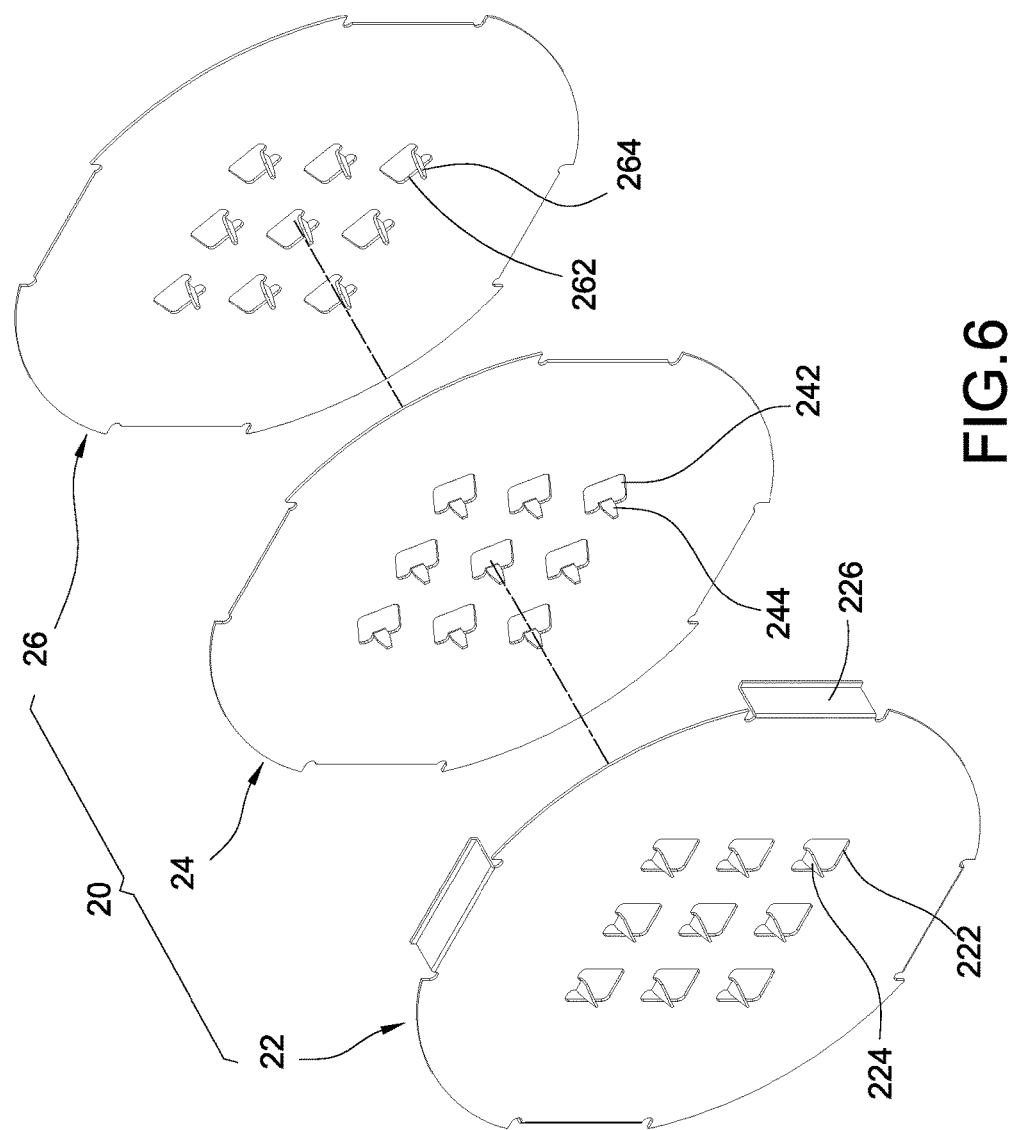
FIG. 6 shows an exploded view of the transdermal microneedle unit according to another embodiment of the present invention from a front viewing direction, wherein every barbule has the same aspect on a sheet.
Figure 7:
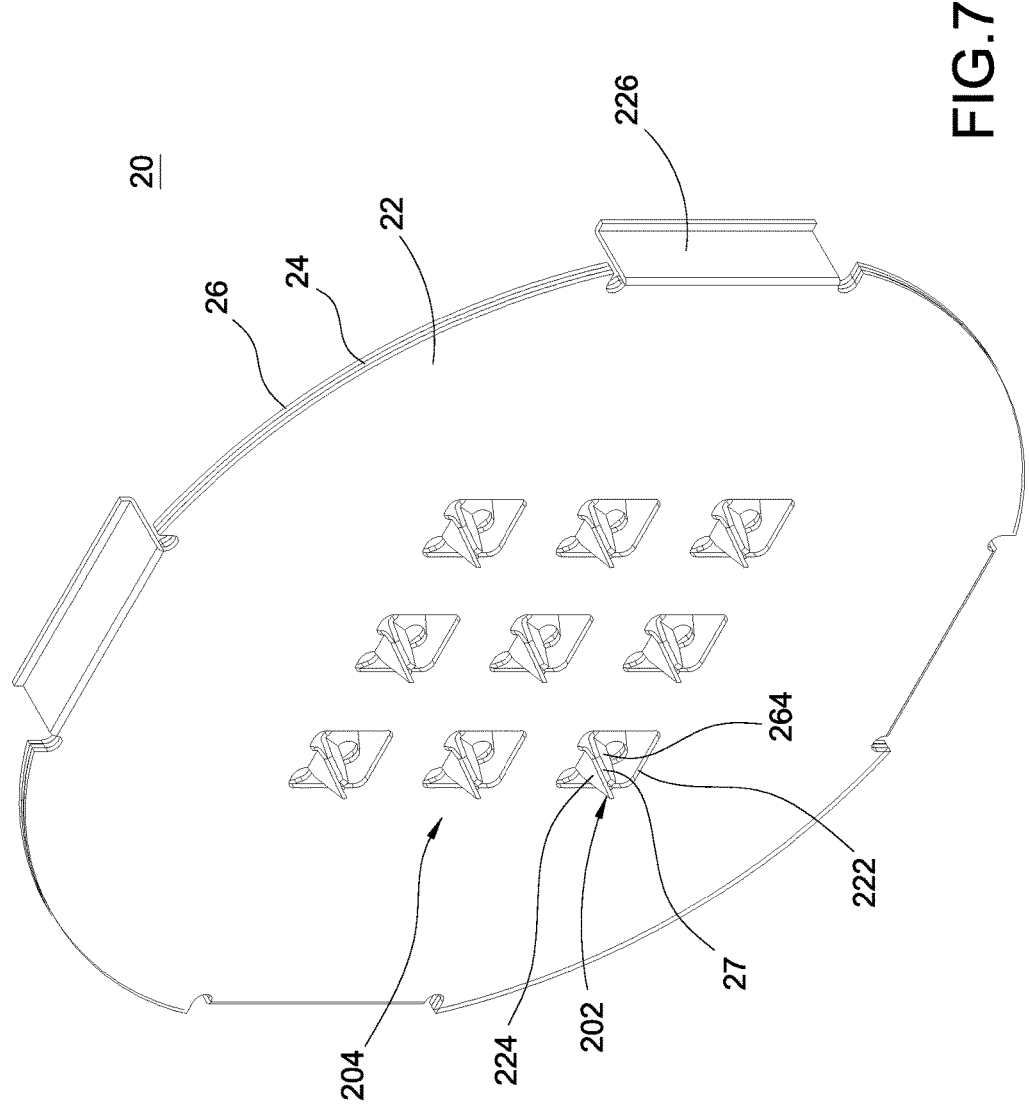
FIG. 7 shows an assembled view of the transdermal microneedle unit of FIG. 6.

Next, please refer to FIG. 6 and FIG. 7. FIG. 6 shows an exploded view of the transdermal microneedle unit according to another embodiment of the present invention from a front viewing direction, wherein every barbule has the same aspect on a sheet. FIG. 7 shows an assembled view of the transdermal microneedle unit of FIG. 6. In an embodiment, the transdermal microneedle unit 20 comprises a first sheet 22, a second sheet 24 and a third sheet 26 stacked with each other. Each of the first sheet 22, the second sheet 24 and the third sheet 26 has array-arranged through holes 222, 242, 262 defined thereon, and a first barbule 224 at peripheral of the first through hole 222, a second barbule 244 at peripheral of the second through hole 242 and a third barbule 264 at peripheral of the third through hole 262. The second array-arranged barbules 244 of the second sheet 24 and the third array-arranged barbules 264 of the third sheet 26 penetrate the first array-arranged through holes 222 of the first sheet 22 in correspondent position to juxtapose the first array-arranged barbules 224 for forming an array-arranged transdermal microneedle 204 as shown in FIG. 7.

Please refer to FIG. 7 again. In another embodiment, the transdermal microneedle unit 20 of the present invention can combine with the latter-mentioned substrate, and the transdermal microneedle 202 of the transdermal microneedle unit 20 is formed of a first barbule 224, a second barbule 244 and a third barbule 264, and there is a space 27 surrounded by the first barbule 224, the second barbule 244 and the third barbule 264. The space 27 can be embedded with a low flowability medication. The barbules are hard, and particularly may made by stainless steel having a thickness less than 0.05 mm to increase the space that can contain medication. Because the surfaces of the barbules are not required to be electroplated with gold or silver, the cost can be greatly reduced, and the transdermal microneedle unit 20 can have more feeding area, for example area of 1 cm×1 cm with 3×3, 4×4, 5×5, 6×6, 7×7 and 8×8 array-arranged micro-needles, or 4×4 array-arranged micro-needles having only 12 micro-needles at four edges or micro-needles arranged circularly, or area of 2 cm×2 cm with 16×16 array-arranged micro-needles. The dose of the array-arranged micro-needles can be increased. The array-arranged micro-needles can be used to deliver pain-killer, e.g., morphine since it is discarded to avoid infection. Also, the array-arranged micro-needles can be used to deliver chronic medications, e.g., alternatives of smoking addition.

Figure 8:
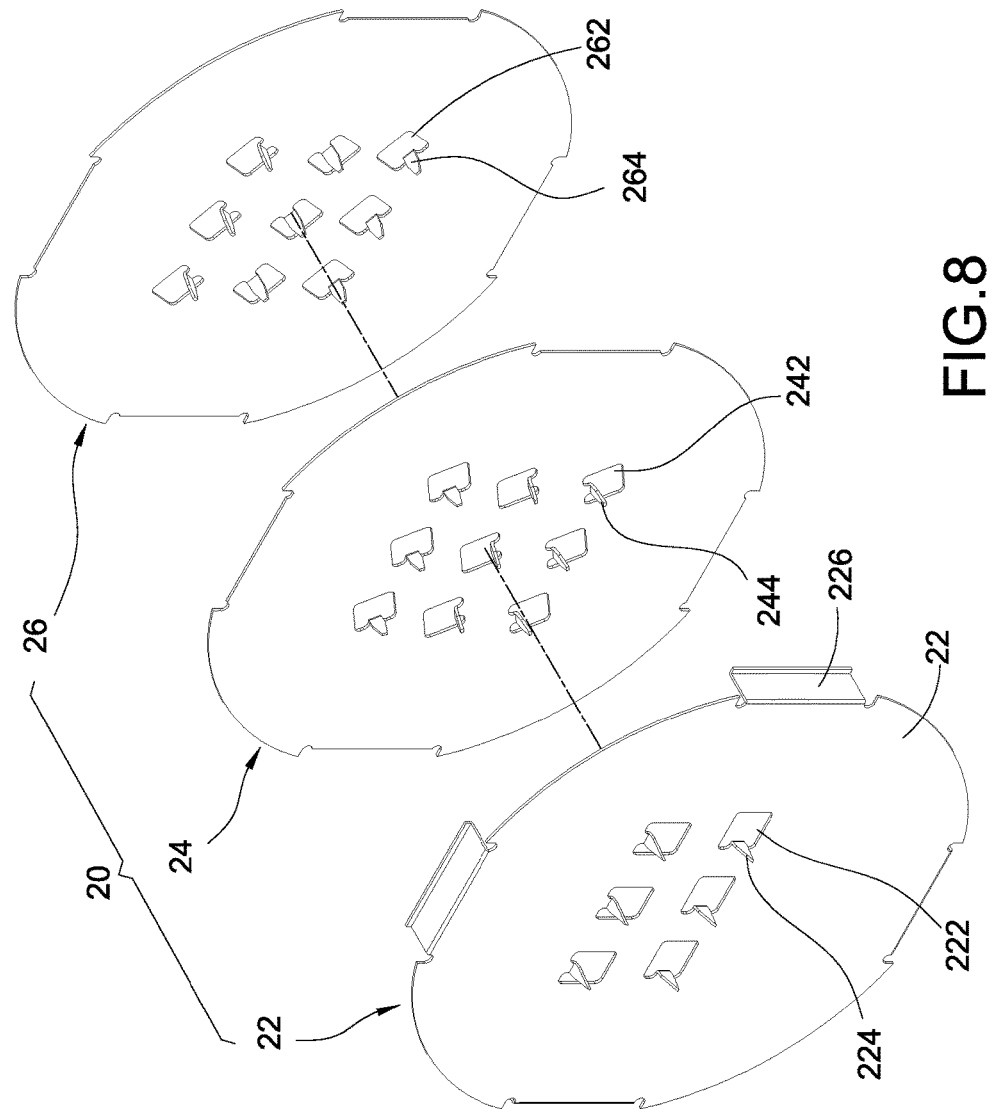
FIG. 8 shows an exploded view of another transdermal microneedle unit according to an embodiment of the present invention from a front viewing direction, wherein barbules in different row have different aspects on a sheet.

FIG. 8 shows an exploded view of another transdermal microneedle unit according to an embodiment of the present invention from a front viewing direction, wherein barbules in different row have different aspects on a sheet. The difference between FIG. 8 and FIG. 6 is that an embodiment of FIG. 8 has the barbules in different row have different aspects on a sheet.

Figure 9:
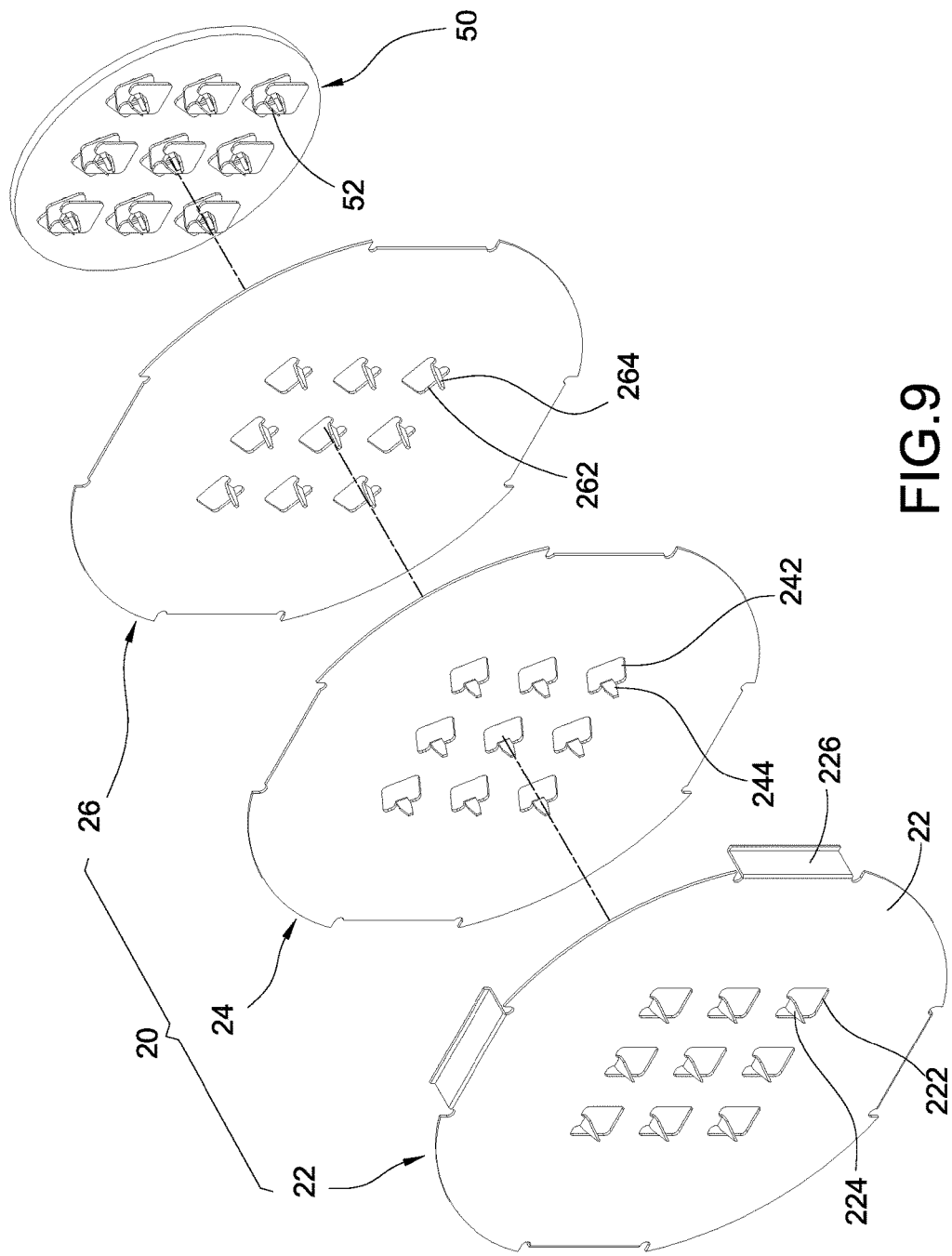
FIG. 9 shows an exploded view of the transdermal microneedle unit and a gasket according to an embodiment of the present invention from a front viewing direction, wherein the gasket is an insert molding article formed by injection molding.
Figure 10:
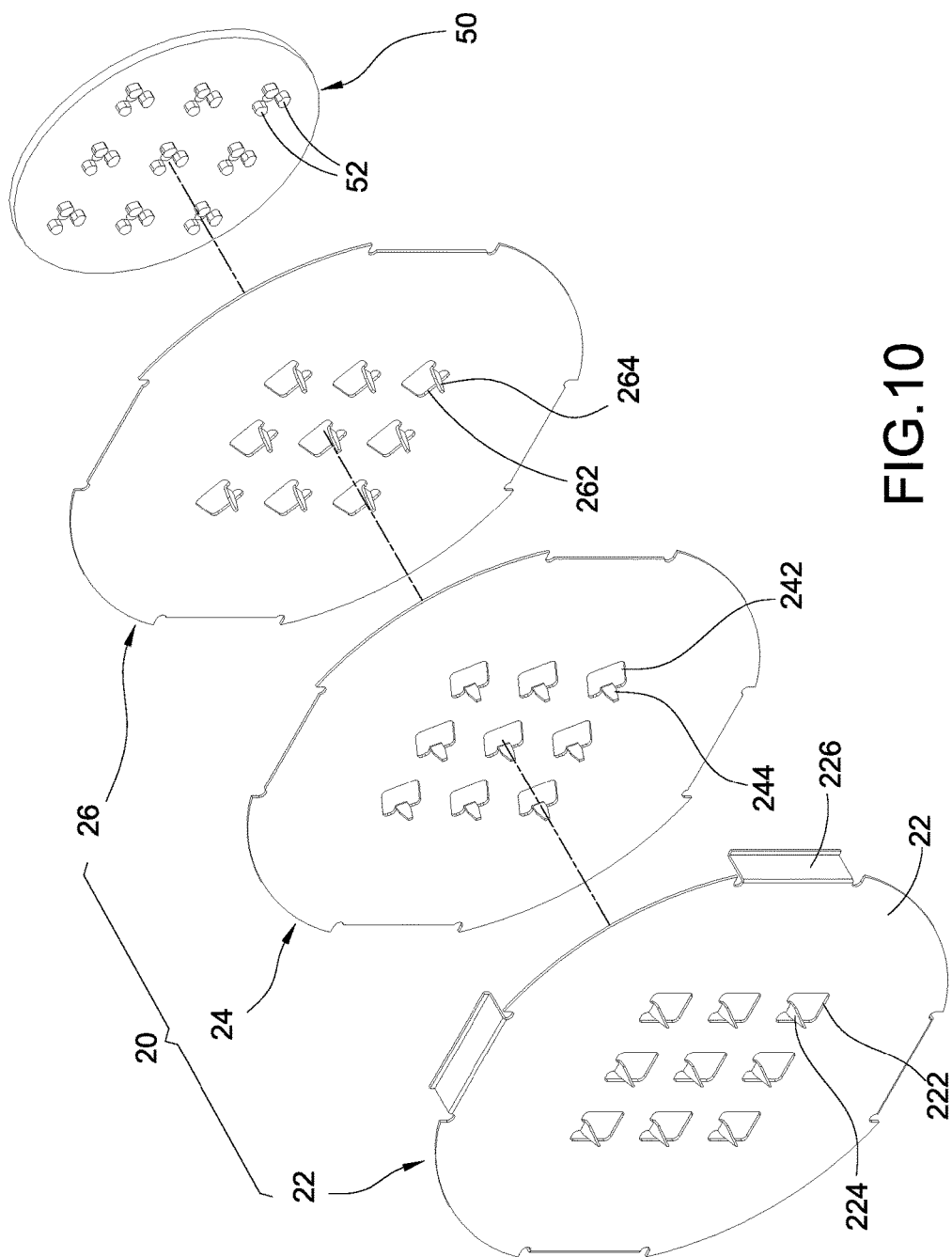
FIG. 10 shows an exploded view of the transdermal microneedle unit and a gasket according to an embodiment of the present invention from a front viewing direction, wherein the gasket is an independent molding article for combining with the transdermal microneedle unit.
Figure 11:
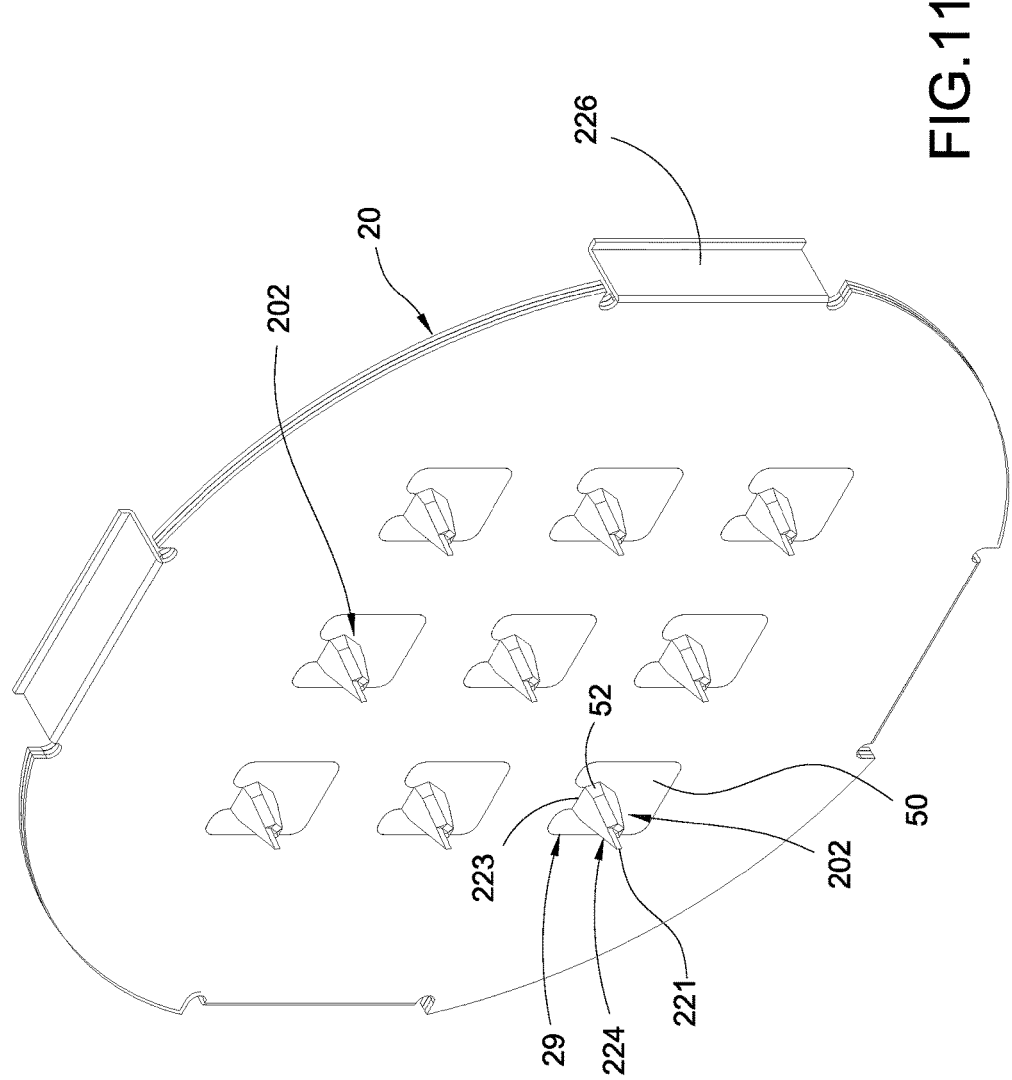
FIG. 11 shows an assembled view of a first sheet, second sheet and third sheet of the transdermal microneedle unit and a gasket according to an embodiment of the present invention from a front viewing direction.

Please refer to FIGS. 9, 10 and 11. FIG. 9 shows an exploded view of the transdermal microneedle unit and a gasket according to an embodiment of the present invention from a front viewing direction, wherein the gasket is an insert molding article formed by injection molding. FIG. 10 shows an exploded view of the transdermal microneedle unit and a gasket according to an embodiment of the present invention from a front viewing direction, wherein the gasket is an independent molding article for combining with the transdermal microneedle unit. FIG. 11 shows an assembled view of a first sheet, second sheet and third sheet of the transdermal microneedle unit and a gasket according to an embodiment of the present invention from a front viewing direction. FIGS. 9 and 10 have the transdermal microneedle unit 20 the same with that of FIG. 6. In an embodiment of FIGS. 9 and 10, the transdermal microneedle unit 20 comprises a first sheet 22, a second sheet 24 and a third sheet 26 stacked with each other. Each of the first sheet 22, the second sheet 24 and the third sheet 26 has array-arranged through holes 222, 242, 262 defined thereon, and a first barbule 224 at peripheral of the first through hole 222, a second barbule 244 at peripheral of the second through hole 242 and a third barbule 264 at peripheral of the third through hole 262. The second array-arranged barbules 244 of the second sheet 24 and the third array-arranged barbules 264 of the third sheet 26 penetrate the first array-arranged through holes 222 of the first sheet 22 in correspondent position to juxtapose the first array-arranged barbules 224 for forming an array-arranged transdermal microneedle.

Please refer to FIG. 11 again. The transdermal microneedles 202 of the transdermal microneedle unit 20 can be arranged to form 3×3 array-arranged micro-needles. In addition, the barbs 226 may be provided on the edge of the first sheet 22 to engage with the grooves 105 of the latter-mentioned substrate 10.

Please refer to FIGS. 9 and 11 again. In an embodiment, the gasket 50 has at least one projecting part 52. The transdermal microneedle unit 20 has an opening 29 on the bottom through where the projecting part 52 of the gasket 50 may penetrate to seal the opening 29 effectively in order to avoid a leakage of medications. According to FIG. 9, the gasket 50 is made by injection molding to combine with the transdermal microneedle unit 20 simultaneously. In other words, the gasket 50 is an insert molding article which can combine with the transdermal microneedle unit 20 closely to avoid a leakage of medications from the opening 29. Alternatively, according to FIG. 10, after the gasket 50 is molded independently, the gasket 50 may combine with the transdermal microneedle unit 20 to avoid a leakage of medications from the opening 29.

Figure 12:
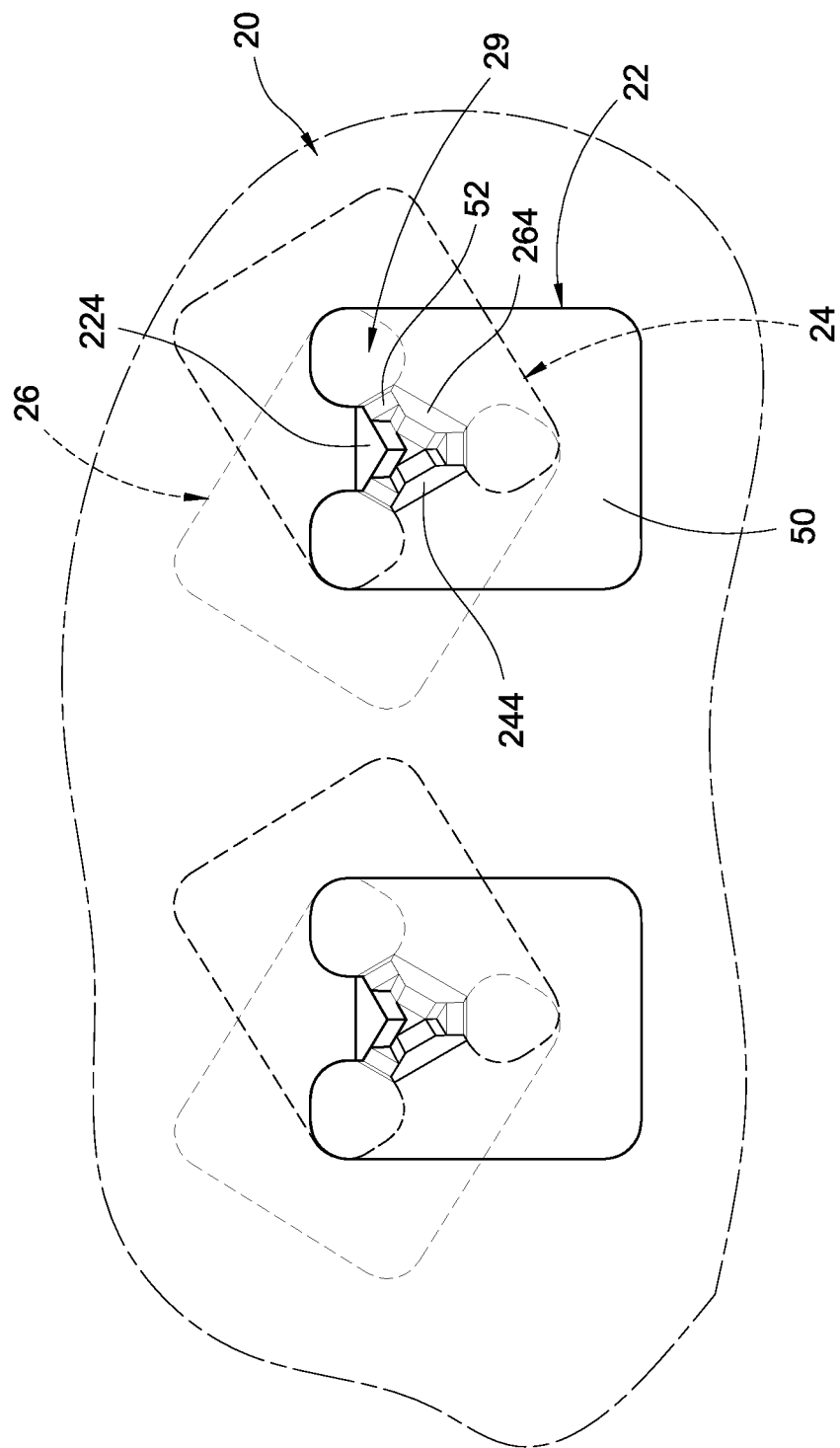
FIG. 12 shows a top view of an assembled view of a first sheet, second sheet and third sheet of the transdermal microneedle unit and a gasket according to an embodiment of the present invention.

FIG. 12 shows a top view of an assembled view of a first sheet, second sheet and third sheet of the transdermal microneedle unit and a gasket according to an embodiment of the present invention. According to FIG. 12, the relationship of position of the first sheet 22, the second sheet 24 and the third sheet 26 as well as the gasket 50 is clear. The transdermal microneedle unit 20 has an opening 29 on the bottom through where the projecting part 52 of the gasket 50 may penetrate to seal the opening 29 effectively in order to avoid a leakage of medications.

Figure 13:
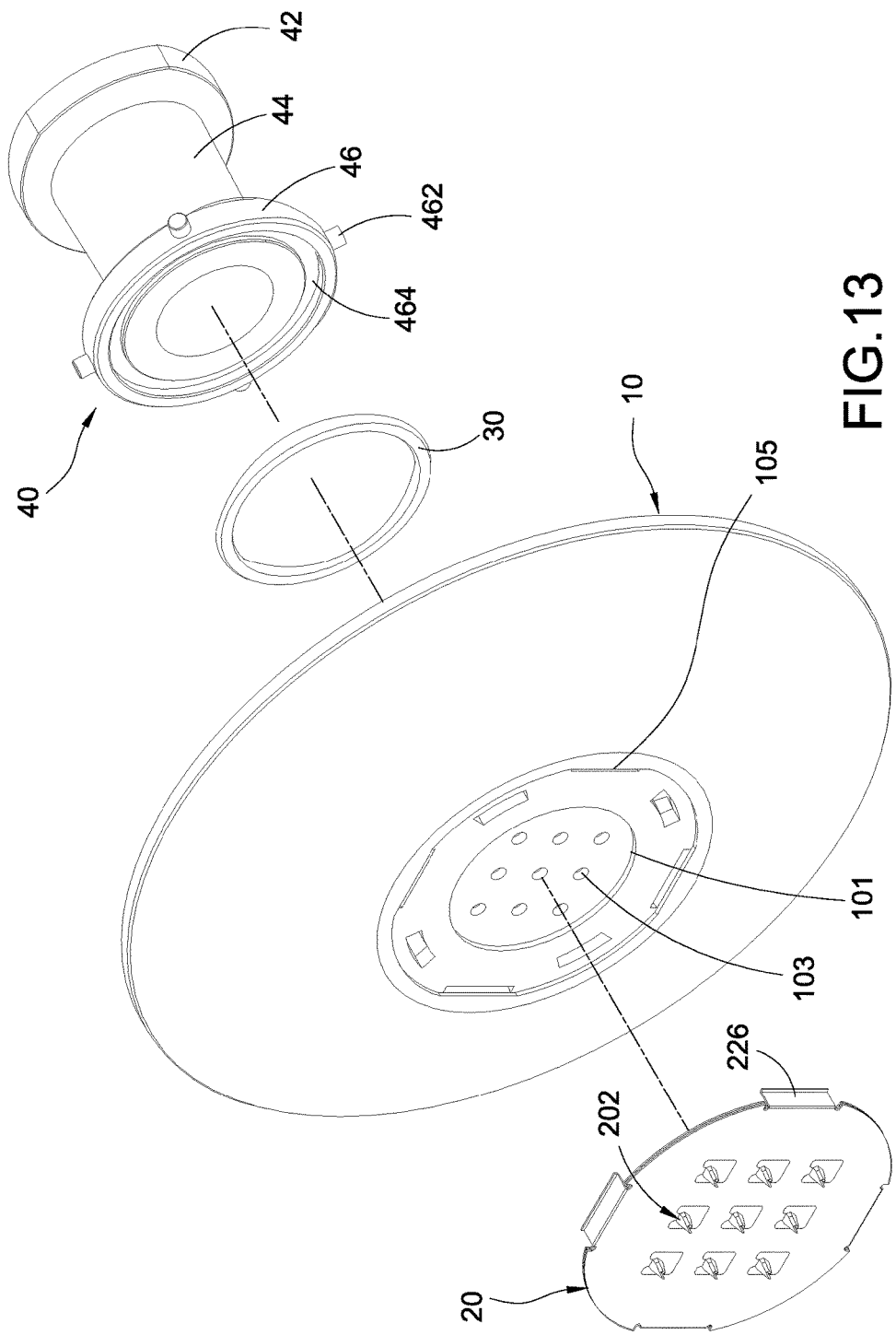
FIG. 13 shows an exploded view of a transdermal microneedle drug delivery device according to an embodiment of the present invention from a front viewing direction.
Figure 14:
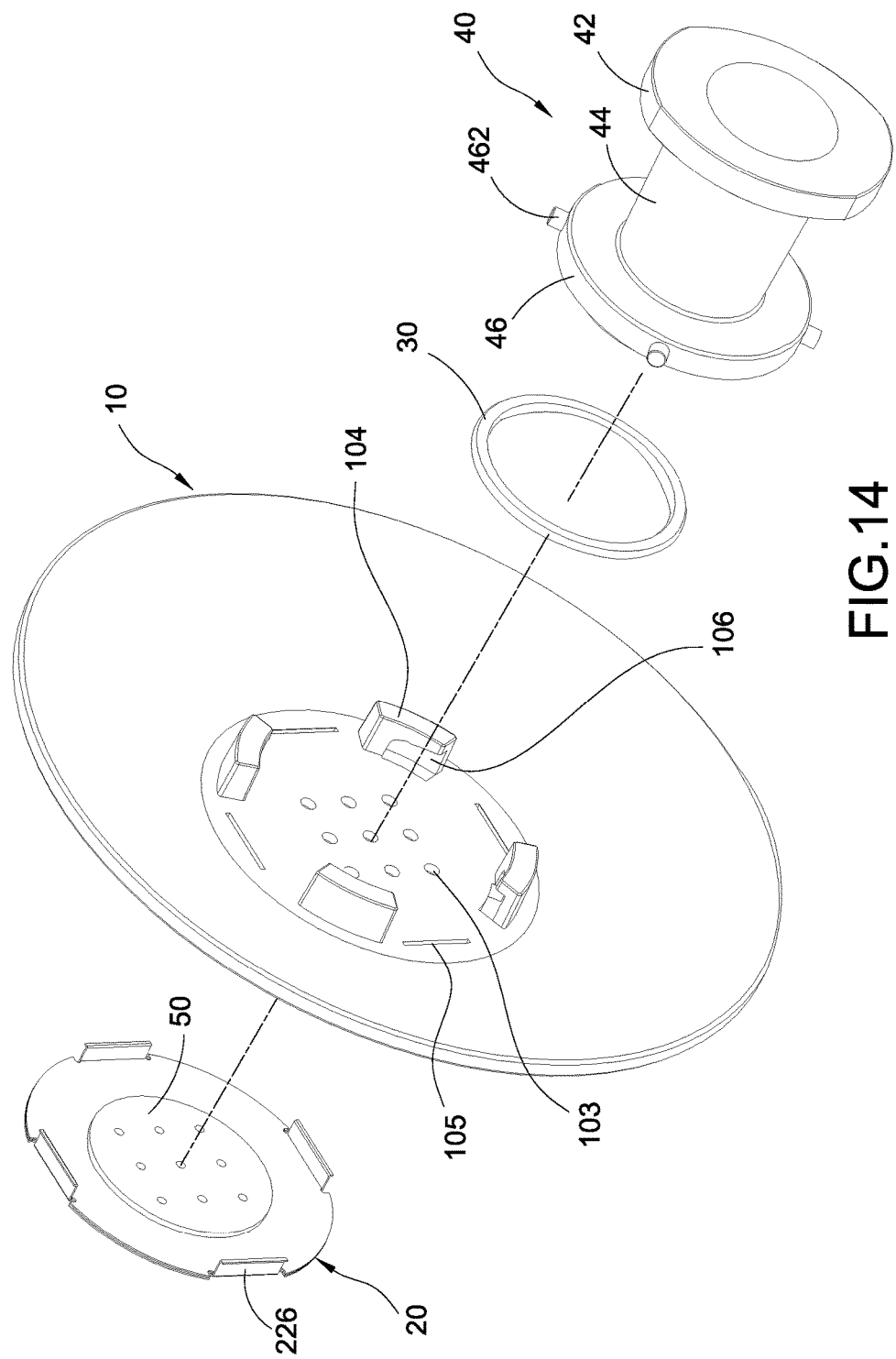
FIG. 14 shows an exploded view of a transdermal microneedle drug delivery device according to an embodiment of the present invention from a rear viewing direction.

FIG. 13 shows an exploded view of a transdermal microneedle drug delivery device according to an embodiment of the present invention from a front viewing direction. FIG. 14 shows an exploded view of a transdermal microneedle drug delivery device according to an embodiment of the present invention from a rear viewing direction. In an embodiment, the transdermal microneedle drug delivery device comprises a substrate 10, a transdermal microneedle unit 20, a O-ring 30 and a union joint 40, wherein the O-ring 30 is provided on a front surface of a front end 46 of the union joint 40.

The substrate 10 has a plurality of holes 103 in a central region 101, in which the holes may be arranged in a 3×3 array to correspond to transdermal microneedles 202 with 3×3 array-arranged micro-needles of the transdermal microneedle unit 20. The substrate 10 has four grooves 105 at perimeter of the central region 101 for providing the transdermal microneedle unit 20. For example, the barbs 226 may be provided on the edge of the first sheet 22 to engage with the grooves 105 of the latter-mentioned substrate 10. In addition, the substrate 10 has a plurality of latches 104, and each of latches 104 has an entrance 106 at an end thereof. The union joint 40 has a plurality of projections 462 at a side surface of a front end 46. The union joint 40 may engage with the substrate 10 by screwing each of projections 462 into the corresponding entrances 106 of the latches 104.

As shown in FIG. 13, the union joint 40 has a front end 46, a middle section 44 and a rear end 42. The front end 46 of the union joint 40 has a circular groove 464 in the front surface for providing the O-ring 30 therein to avoid a leakage of medications. The union joint 40 may engage with the substrate 10 by the front end 46, and may engage with an injection syringe (not shown in FIGS. 13 and 14) by the rear end 42 for applying the medications into skin.

Figure 15:
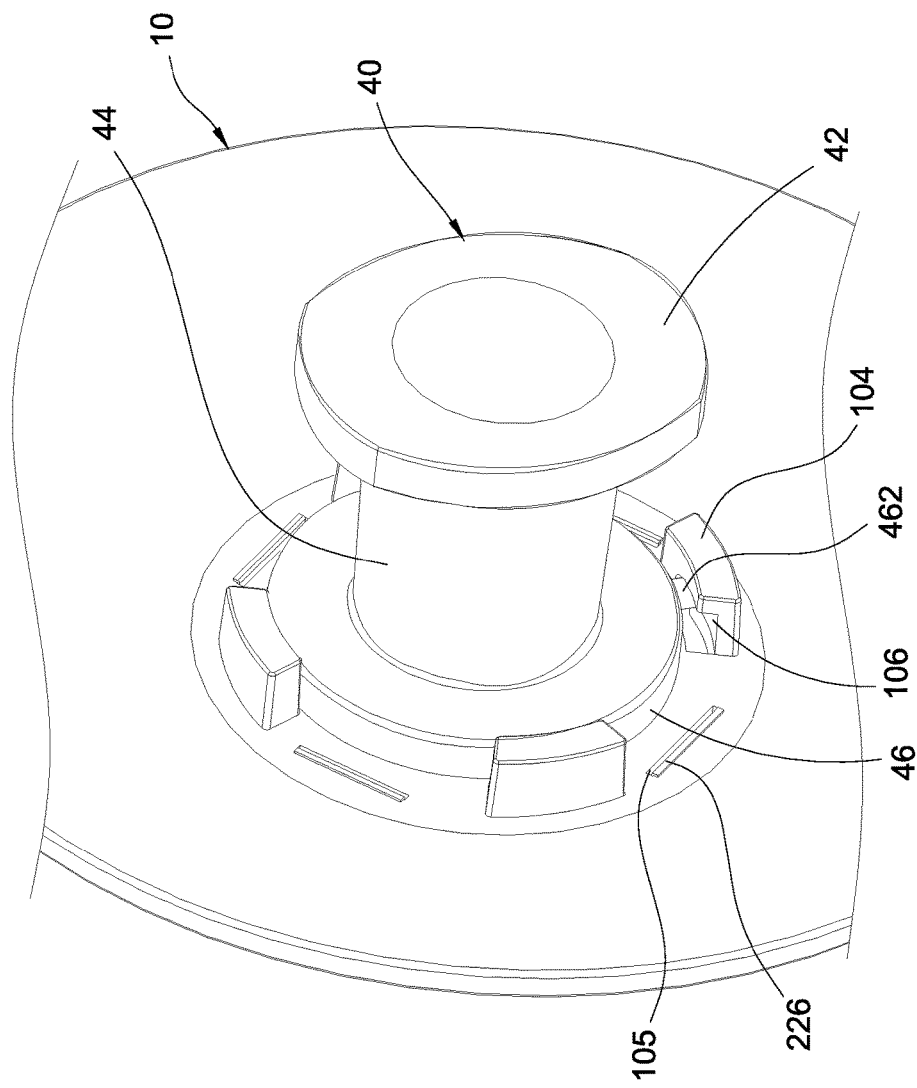
FIG. 15 shows an assembled view of a substrate and a union joint according to an embodiment of the present invention from a rear viewing direction.

FIG. 15 shows an assembled view of a substrate and a union joint according to an embodiment of the present invention from a rear viewing direction. As shown in FIG. 15, the union joint 40 has a front end 46, a middle section 44 and a rear end 42. In addition, the substrate 10 has four latches 104, and each of latches 104 has an entrance 106 at an end thereof. The union joint 40 has four projections 462 at a side surface of a front end 46. The union joint 40 may engage with the substrate 10 by screwing each of projections 462 into the corresponding entrances 106 of the latches 104.

Figure 16:
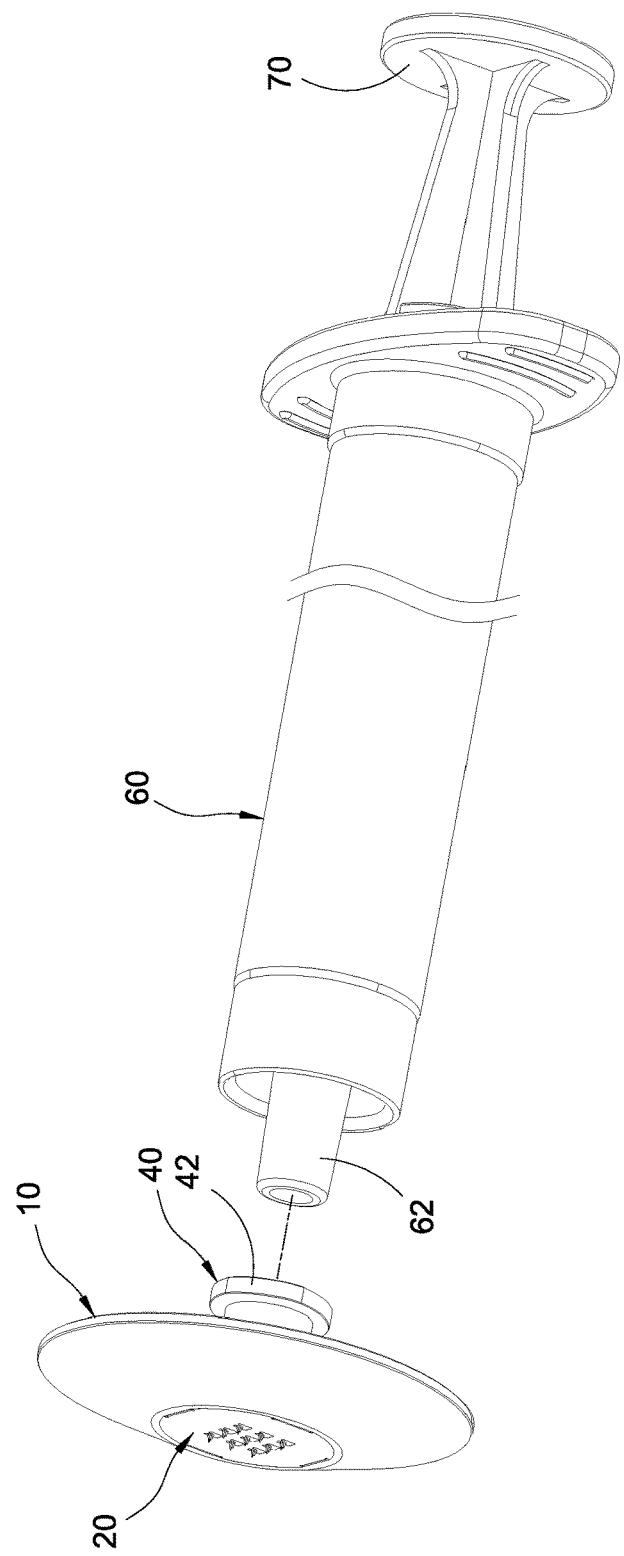
FIG. 16 shows a schematic view of a transdermal microneedle drug delivery device and an injection syringe in disassembled state according to an embodiment of the present invention.

FIG. 16 shows a schematic view of a transdermal microneedle drug delivery device and an injection syringe in disassembled state according to an embodiment of the present invention. In an embodiment, the transdermal microneedle drug delivery device further comprises an injection syringe 60 including a plunger 70. The injection syringe 60 has a connecting end 62 for connecting with the rear end 42 of the union joint 40, and the plunger 70 can be pushed along inside a cylindrical tube of the injection syringe 60 to apply the medications into skin through the transdermal microneedle unit 20 engaged with the substrate 10. In operation, firstly a standard needle is connected to the injection syringe 60, and medication is drawn out from a medicine bottle by pulling the plunger 70 along inside a cylindrical tube of the injection syringe 60. Next, the standard needle is removed, and the transdermal microneedle unit 20 engaged with the substrate 10 is provided to apply the medication into skin. In an embodiment, the transdermal microneedle drug delivery device comprising an injection syringe 60 and a plunger 70 further includes prefilled medication so that it may directly apply the medication into skin.

Figure 17:
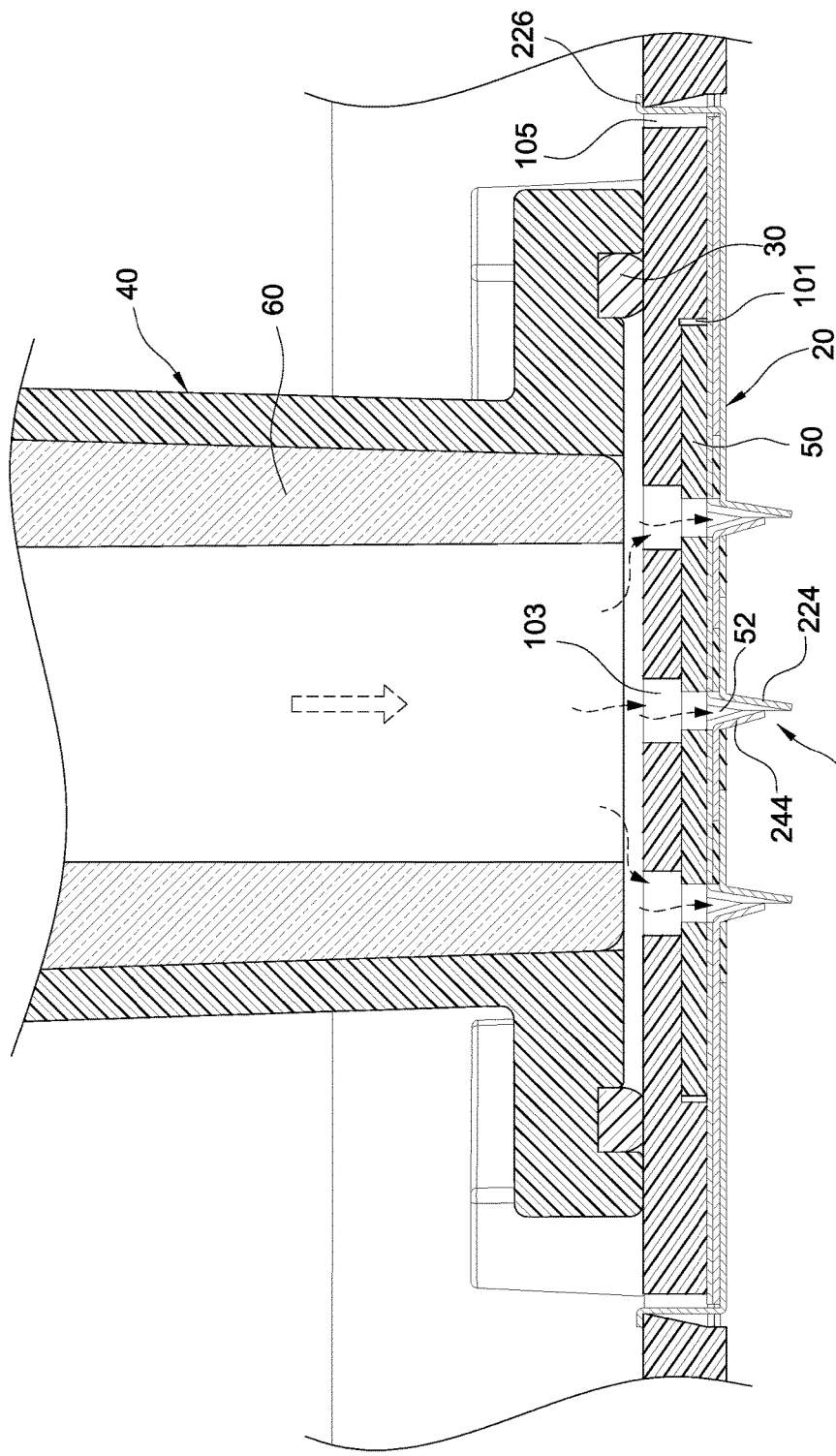
FIG. 17 shows a sectional assembled view of a transdermal microneedle drug delivery device and an injection syringe for applying drug according to an embodiment of the present invention.

FIG. 17 shows a sectional assembled view of a transdermal microneedle drug delivery device and an injection syringe for applying drug according to an embodiment of the present invention. In an embodiment, the transdermal microneedle drug delivery device comprises a substrate 10, a transdermal microneedle unit 20 and a union joint 40. The substrate 10 has a plurality of holes 103 in a central region 101, in which the holes 103 may be arranged in a array to correspond to transdermal microneedles 202 with array-arranged micro-needles of the transdermal microneedle unit 20, wherein the transdermal microneedle 202 comprises a first barbule 224, a second barbule 244 and a third barbule (not shown in FIG. 17). The projecting part 52 of the gasket 50 may penetrate to seal the opening on the bottom of the transdermal microneedle unit 20 effectively in order to avoid a leakage of medications. Also, the O-ring 30 is provided on a front surface of a front end of the union joint 40. The barbs 226 may be provided on the edge of the first sheet 22 to engage with the grooves 105 of the substrate 10. The injection syringe 60 has a connecting end for connecting with the rear end of the union joint 40, and the plunger can be pushed along inside a cylindrical tube of the injection syringe 60 to apply the medications into skin through the transdermal microneedle unit 20 engaged with the substrate 10.

In another embodiment, the transdermal microneedle drug delivery device may comprise a micropump and a micro control unit. The micropump is connected with the rear end of the union joint, and the micropump is driven by a signal produced from the micro control unit to apply the medications into skin.

In an embodiment, the transdermal microneedle drug delivery device may be used in a continue type or a close loop in accordance with mechanisms of drug metabolism of a patient. The accurate drug delivery of a close loop can be achieved in combination of a micro sensor of detecting the concentration of drug in the body of the patient.

The invention is not limited to these embodiments, but various variations and modifications may be made without departing from the scope of the invention.

What is claimed is:

1. A transdermal microneedle drug delivery device, comprising:
    a substrate;
    a transdermal microneedle unit, provided on the substrate, the transdermal microneedle unit comprising at least two sheets stacked with each other, each of the at least two sheets having at least one through hole defined thereon and a barbule arranged at a periphery of the through hole, wherein the through hole on one of the at least two sheets is penetrated by the barbules of another one of the at least two sheets, and tips of the barbules are in a polygon arrangement from top view;
    a union joint, connected with the substrate by an end thereof; and
    a gasket, the gasket having at least one projecting part disposed between any two adjacent barbules that juxtapose with each other to form a transdermal microneedle for sealing an opening of the transdermal microneedle of the transdermal microneedle unit.

2. The transdermal microneedle drug delivery device in claim 1, wherein the substrate has a plurality of latches, and each of latches has an entrance at an end thereof, and the union joint has a plurality of projections at a side surface of an end, and the union joint is engaged with the substrate by screwing each of projections into the corresponding entrances of the latches.

3. A transdermal microneedle drug delivery device, comprising:
    a substrate;
    a transdermal microneedle unit, provided on the substrate, the transdermal microneedle unit comprises at least two sheets stacked with each other, each of the at least two sheets having array-arranged through holes defined thereon and a barbule arranged at a periphery of each of the through holes in array arrangement, wherein each of the array-arranged through holes on one of the at least two sheets is penetrated by the barbules of another one of the at least two sheets, and tips of the barbules are in a polygon arrangement from top view;
    a union joint, connected with the substrate by an end thereof; and
    a gasket, the gasket having at least one projecting part disposed between any two adjacent barbules that juxtapose with each other to form a transdermal microneedle for sealing an opening of the transdermal microneedle of the transdermal microneedle unit.

4. The transdermal microneedle drug delivery device in claim 3, wherein the substrate has a plurality of latches, and each of latches has an entrance at an end thereof, and the union joint has a plurality of projections at a side surface of an end, and the union joint is engaged with the substrate by screwing each of projections into the corresponding entrances of the latches.

5. The transdermal microneedle drug delivery device in claim 4, wherein the union joint has a circular groove in a front surface of an end thereof.

6. The transdermal microneedle drug delivery device in claim 5, further comprising an O-ring which is provided in the circular groove of the union joint.

7. The transdermal microneedle drug delivery device in claim 3, further comprising an injection syringe including a plunger, in which the injection syringe has a connecting end for connecting with an end of the union joint, and the plunger is pushed along inside a cylindrical tube of the injection syringe to apply medications into skin.

* * * * *